United States Patent [19]

Saqualain Haider Rizvi et al.

[11] Patent Number: 5,728,912
[45] Date of Patent: Mar. 17, 1998

[54] BUTENE-1 PRODUCTION BY DIMERIZATION OF ETHYLENE COMPRISING AN IMPROVED SPENT CATALYST REMOVAL SECTION

[75] Inventors: Syed Saqualain Haider Rizvi, Hicksville, N.Y.; Fahad Abdulaziz Al Sherehy; Moayyed Issa Al-Qurtas, both of Riyadh, Saudi Arabia; Alain Forestiere, Vernaison; Jean Gaillard, Lyons, both of France

[73] Assignees: Institut Francais du Petrole, Rueil Malmaison, France; Saudi Basic Industries Corp., Riyadh, Saudi Arabia

[21] Appl. No.: 639,610

[22] Filed: Apr. 29, 1996

[30] Foreign Application Priority Data

Apr. 28, 1995 [FR] France .................... 95 05252

[51] Int. Cl.$^6$ .................................................. C07C 3/21
[52] U.S. Cl. ............... 585/512; 585/510; 585/524; 502/126
[58] Field of Search ................ 585/512, 524, 585/510, 504, 511, 902, 904, 22, 523, 922; 502/126

[56] References Cited

U.S. PATENT DOCUMENTS 4,532,370  7/1985  Lé Quan et al. ............... 585/512
4,615,998  10/1986  Le Quan et al. .............. 502/126
5,001,274  3/1991  Bunning ......................... 568/454

Primary Examiner—Glenn Caldarola
Assistant Examiner—Bekir L. Yildirim
Attorney, Agent, or Firm—Millen, White, Zelano, & Branigan, P.C.

[57] ABSTRACT

The process of butene-1 production comprises the steps of: a) sending a inhibited catalyst containing reactor effluent to a flash section where the pressure is decreased by about 0.1 MPa to about 2 MPa, and obtaining a first gaseous phase containing ethylene and butene-1 and a first liquid phase containing the inhibited catalyst; b) sending the first liquid phase from step a) to at least one vaporisation section which allows the separation of a second gaseous phase containing butene-1 and ethylene from a second liquid phase containing the inhibited catalyst; c) sending the second liquid phase from step b) to at least one thin film evaporation section which allows the separation of a third gaseous phase containing ethylene, butene-1 and some other heavier hydrocarbon products from a concentrated inactivated catalyst solution and, d) collecting the first, second and third gaseous phases to form a gaseous reactor effluent substantially free of spent catalyst.

8 Claims, No Drawings

BUTENE-1 PRODUCTION BY DIMERIZATION OF ETHYLENE COMPRISING AN IMPROVED SPENT CATALYST REMOVAL SECTION

The object of the present invention is an improved industrial process for the manufacture of butene-1 from ethylene.

Many patents describe methods for synthesising butene-1 by dimerization of ethylene. Among these patents the U.S. Pat. No. 4,532,370 assigned to IFP describes a very high activity and selectivity catalyst for butene-1. In the process however, the spent catalyst must be deactivated and then removed from the reactor effluent by vaporising almost all of the effluent. The catalyst removal section needs special vaporising equipment such as for example thin film evaporators to vaporise the desired product.

The object of the present invention is to provide an improved process for manufacture of butene-1 by dimerization of ethylene comprising a very efficient catalyst removal section. The process of the invention in which about 99 wt % of the reactor effluent is vaporised in two stages, first using an ordinary vaporiser and then thin film evaporator, has the advantage of limiting vaporisation duty on the thin film evaporator. This limitation decreases the plant cost significantly. Moreover, the vaporisation at high temperatures and pressures causes frequent fouling of vaporiser due to polymer properties modification at high temperature in the vaporiser. In the process of the invention, high temperatures are avoided so that fouling of the vaporiser is efficiently limited. Another very important advantage of the process of the present invention results from the possibility of using one or more thin film evaporators of limited size which leads to a limited plant cost.

The invention thus concerns an improved process of making butene-1 by liquid phase homogeneous catalytic dimerization of ethylene, under a pressure between 0.5 MPa and 8 MPa with a temperature between 20° C. and 150° C., comprising a step of contacting a dimerization reactor effluent with a catalyst inhibitor and a step of recovering a substantially catalyst free reactor effluent and a concentrated inactivated catalyst solution, said process is characterized by the steps of:

a) sending a inhibited catalyst containing reactor effluent to a flash section where the pressure is decreased of about 0.1 MPa to about 2 MPa, and obtaining a first gaseous phase containing ethylene and butene-1 and a first liquid phase containing the inhibited catalyst, b) sending the first liquid phase from step a) to at least one vaporisation section where it is vaporised under substantially the same pressure as in step a) and under a temperature which allows the separation of a second gaseous phase containing butene-1 and ethylene from a second liquid phase containing the inhibited catalyst, c) sending the second liquid phase from step b) to at least one thin film evaporation section where it is evaporated under substantially the same pressure as in steps b) under conditions which allow the separation of a third gaseous phase containing ethylene, butene-1 and some other heavier hydrocarbon products from a concentrated inactivated catalyst solution, and d) collecting the first, second and third gaseous phases to form a gaseous reactor effluent substantially free of spent catalyst.

In the dimerization process of ethylene, the reactor effluent always contains some heavy components such as C6 (mainly olefinic compounds) and C6+ (mainly octene) formed by side reaction in the reactor. The catalyst remains dissolved in this heavy fraction and will be removed as a solution in this fraction.

During the dimerization of ethylene, the reactor pressure is preferably between 1.5 MPa and 3 MPa and the temperature preferably between 30° C. and 70° C. and more preferably from about 50° C. to about 70° C. The reactor effluent is contacted with a sufficient quantity of a catalyst inhibitor such for example an oxygen polar or a nitrogen polar compound to substantially deactivate the whole catalyst present in the effluent before sending this effluent to the flash section. Such nitrogen catalyst inhibitors are for example described in the european patent EP-B-200 654.

Within the flash section, the pressure from the reactor effluent will be preferably decreased by about 0.5 MPa to about 1 MPa. In this section, due to the pressure reduction, a part of the effluent is vaporised. Generally the pressure drop is such that at least 5 wt %, for example 8 a 15%, of the effluent coming from the reactor are vaporised.

The first liquid phase obtained in the flash section is sent to the vaporisation section which comprises one or more vaporisers. In this vaporisation section, the temperature is preferably between 60° C. and 100° C. and more preferably between 70° C. and 90° C. Under these conditions, at least 50 wt %, for example 55% to 81%, of the reactor effluent are vaporised in this section.

The second liquid phase recovered after the vaporisation section is sent to a thin film evaporation section which comprises at least one thin film evaporator and often two or more substantially identical thin film evaporators. In this section, at most 25 wt %, for example 10 to 20% of the reactor effluent are generally vaporised.

In a preferred embodiment, the gaseous, substantially catalyst free reactor effluent is condensed to a liquid product which can be sent to a separation section where butene-1 is separated from ethylene. The condensation is generally done at the pressure of the gaseous product collected after each vaporisation step of the present invention. The liquid product obtained can be then pressurised to a pressure substantially identical to the dimerization reactor pressure. This pressurisation could be done with a centrifugal pump or any other apparatus well known in the art.

The success of this new process scheme depends on the concentration of ethylene in the reactor effluent and how the maximum vaporisation duty can be shifted towards vaporiser rather than towards thin film evaporators. Obviously, the vaporiser operating pressure plays a key rule by shifting the vaporisation duty. The butene-1 process requires almost total vaporisation of reactor effluent in order to remove the catalyst from the effluent and then total condensation before the distillation train. A low operating pressure favours vaporisation of the reactor effluent in the vaporiser while a high operating pressure favours recondensation of the reactor effluent in the recycle column feed condenser, especially when the concentration of ethylene is higher in the reactor effluent. This invention is based on the optimisation of these vaporisation and condensation pressures.

According to this invention, a thin film evaporator is used to only remove a small amount of dissolved catalyst; therefore, an unnecessary liquid flow to thin film evaporator is avoided. The catalyst purge from the bottom of the thin film evaporator contains about 13 wt %, for example, of unvapourisable catalyst.

The refrigeration duty required for the new process is minimised by optimising the cooling and chilled water flows and rearranging the pump-around coolers and recycle column feed condensers. A minimum chilled water temperature is desirable to condense all of the vapours produced in the catalysts removal section. The butene-1 reactor can be operated under such conditions that the ethylene concentration in the reactor effluent is 10 to 15 wt %, for example. At this low concentration of ethylene, after removing the catalyst, the reactor effluent can be recondensed, for example, at 1.3 MPa and 15° C. This recondensed liquid is the thin film evaporators are then mixed to form a gaseous stream and then passed through two condensers connected in series. All the vapours are condensed at 1.31 MPa and 15° C. The 15° C. condenser outlet temperature limitation is imposed by the available chilled water temperature (10° C.). The material balance is shown in table 1 thereafter.

TABLE 1

| REACTOR EFFLUENT | | CATALYST PURGE | | GASEOUS STREAMS | |
|---|---|---|---|---|---|
| COMPONENT | WT % | COMPONENT | WT % | COMPONENT | WT % |
| methane | 0.0338 | methane | 0.0 | methane | 0.0377 |
| ethane | 1.0709 | ethane | 0.0006 | ethane | 1.1019 |
| ethylene | 13.822 | ethylene | 0.0017 | ethylene | 14.135 |
| butene-1 | 79.031 | butene-1 | 13.342 | butene-1 | 79.469 |
| butane | 0.0883 | butane | 0.0175 | butane | 0.0688 |
| hexene-1 | 5.5093 | hexene-1 | 59.401 | hexene-1 | 4.8649 |
| hexane | 0.3039 | hexane | 3.9689 | hexane | 0.2571 |
| octene-1 | 0.1523 | octene-1 | 7.5734 | octene-1 | 0.0615 |
| catalyst inhibitor | 0.0000 | catalyst inhibitor | 2.4614 | catalyst inhibitor | 0.0044 |
| catalyst | 0.1554 | catalyst | 13.234 | catalyst | 0.0 | then pressurised to the desired recycle column operating pressure to separate ethylene from butene-1 and other heavy components.

According to this invention, preferably all the vapours from the catalysts removal section are recondensed at low pressure for example at 1.3 Mpa, because generally a liquid pump is used to raise the pressure of the reactor effluent from the low pressure to the pressure of the dimerization reaction that for example from 1.3 to 2.6 MPa. After fractionation, unreacted ethylene is recycled to the butene-1 reactor which operates for example around 2.3 Mpa.

The following examples illustrate the invention without however limiting the scope thereof.

EXAMPLE 1

This example gives the details of material and energy balances of a butene-1 plant according to this invention. The example covers material and energy balances of 11.7 MT/h butene-1 in the reactor effluent. The dimerization of ethylene is done at a temperature of 53° C. under a pressure of 2.32 MPa in the presence of the catalyst described in the example 1 of the IFP patent U.S. Pat. No. 4,532,370.

The reactor effluent pressure is dropped by 0.77 Mpa (from 2.32 MPa to 1.55 MPa) across a pressure control valve that vaporises about 10.1 wt % of reactor effluent and reduces the reactor effluent temperature by 11° C. (from 53° C. to 42° C.). 5 kg of decylamine as catalyst inhibitor is added to the hot reactor effluent to deactivate the catalyst prior to the depressurising step. The reactor effluent after the depressurising step is sent to a flash drum. The vapour stream, from the upper part, is recovered to be sent to at least one condenser. The liquid from the flash drum is then pumped into a vaporiser. The liquid from the flash drum is heated to 83° C. in the vaporiser. Since the pressure in the vaporiser is only 1.5 MPa, about 69.1 wt % of the reactor effluent is vaporised, at 83° C. This scheme allows 3 MT/h of liquid, containing a small amount of catalyst, to flow to thin film evaporator section consisting of two thin film evaporators in series. The 95 wt % of this liquid is vaporised in the first and second thin film evaporators and about 5 wt % is removed as catalyst purge. The first, second and third streams from respectively the flash drum, the vaporiser and

EXAMPLE 2

In this example the dimerization conditions are identical to those of example 1 but the catalyst removal section pressure is further reduced. The catalyst removal section pressure is further dropped by 0.1 MPa (1 bar) to 1.45 MPa, the liquid flow to thin film evaporator decreases from 3 to 2 MT/h, thus requiring even smaller thin film evaporator. One bar reduction in pressure reduces the thin film evaporator duty by 13%, but the penalty has to be paid insofar as condensation of about 274 kg of vapours at 1.21 MPa and 15° C. is impossible. However, total condensation of these vapours is made at 1.21 MPa by reducing the process side temperature at the condenser outlet to 12° C.

The preceding examples can be repeated with similar success by substituting the generically or specifically described reactants and/or operating conditions of this invention for those used in the preceding examples.

The entire disclosure of all applications, patents and publications, cited above, and of corresponding French application 95/05252, are hereby incorporated by reference.

From the foregoing description, one skilled in the art can easily ascertain the essential characteristics of this invention, and without departing from the spirit and scope thereof, can make various changes and modifications of the invention to adapt it to various usages and conditions.

We claim:

1. Process of making butene-1 by liquid phase homogeneous catalytic dimerization of ethylene, under a pressure between 0.5 MPa and 8 MPa with a temperature between 20° C. and 150° C., comprising a step of contacting a dimerization reactor effluent with a catalyst inhabiter and a step of recovering a substantially catalyst free reactor effluent and a concentrated inactivated catalyst solution, characterized in that said process comprises the steps of:

a) sending a inhibited catalyst containing reactor effluent to a flash section where the pressure is decreased by about 0.1 MPa to about 2 MPa, and obtaining a first gaseous phase containing ethylene and butene-1 and a first liquid phase containing the inhibited catalyst, b) sending the first liquid phase from step a) to at least one vaporisation section where it is vaporised under substantially the same pressure as in step a) and under a temperature which allows the separation of a second gaseous phase containing butene-1 and ethylene from a second liquid phase containing the inhibited catalyst, c) sending the second liquid phase from step b) to at least one thin film evaporation section where it is evaporated under substantially the same pressure as in steps b) under conditions which allow the separation of a third gaseous phase containing ethylene, butene-1 and some other heavier hydrocarbon products from a concentrated inactivated catalyst solution and, d) collecting the first, second and third gaseous phases to form a gaseous reactor effluent substantially free of spent catalyst.

2. The process of claim 1 wherein said gaseous reactor effluent substantially free of spent catalyst is condensed to a liquid product.

3. The process of claim 2 wherein the liquid product is sent to a separation section where butene-1 is separated from ethylene.

4. The process according to claim 1 wherein the dimerization of ethylene is made under a pressure between 1.5 MPa and 3 MPa with a temperature between 30° C. and 70° C.

5. The process according to claim 4 wherein the pressure in the flash section is decreased by about 0.5 MPa to about 1 MPa.

6. The process according to claim 5 wherein the temperature in the vaporisation section is between 60° C. and 100° C.

7. The process according to claim 6 wherein the thin film evaporation section comprises one thin film evaporator.

8. The process according to claim 6 wherein the thin film evaporation section comprises at least two thin film evaporators in series.

* * * * *